(12) United States Patent
Dimitroulis

(10) Patent No.: US 11,364,113 B2
(45) Date of Patent: Jun. 21, 2022

(54) ANCHORED IMPLANT FOR A NASAL PROSTHESIS

(71) Applicant: TMJ ORTHOPAEDICS PTY LTD, East Melbourne (AU)

(72) Inventor: George Dimitroulis, East Melbourne (AU)

(73) Assignee: TMJ ORTHOPAEDICS PTY LTD, East Melbourne (AU)

( * ) Notice: Subject to any disclaimer, the term of this patent is extended or adjusted under 35 U.S.C. 154(b) by 0 days.

(21) Appl. No.: 16/978,850

(22) PCT Filed: Feb. 12, 2019

(86) PCT No.: PCT/AU2019/050107
§ 371 (c)(1),
(2) Date: Sep. 8, 2020

(87) PCT Pub. No.: WO2019/169430
PCT Pub. Date: Sep. 12, 2019

(65) Prior Publication Data
US 2021/0038375 A1    Feb. 11, 2021

(30) Foreign Application Priority Data

Mar. 8, 2018  (AU) ................. 2018900752

(51) Int. Cl.
*A61F 2/18*    (2006.01)
*A61F 2/00*    (2006.01)
*A61F 2/28*    (2006.01)

(52) U.S. Cl.
CPC ............ *A61F 2/186* (2013.01); *A61F 2/0059* (2013.01); *A61F 2/2875* (2013.01); *A61F 2/18* (2013.01);

(Continued)

(58) Field of Classification Search
CPC ...... A61F 2/186; A61F 2/0059; A61F 2/2875; A61F 2002/2885; A61F 2230/0023; A61F 2210/009; A61F 2220/0041; A61F 2/18
See application file for complete search history.

(56) References Cited

U.S. PATENT DOCUMENTS 5,263,980 A    11/1993  Leibinger et al.
5,425,763 A     6/1995  Stemmann
(Continued)

FOREIGN PATENT DOCUMENTS

CN    103070738 B    7/2015
RU     2618891 C1    5/2017

OTHER PUBLICATIONS

Bidra, A. S. et al., 'Maxillofacial Rehabilitation of a Microstomic Patient After Resection of Nose, Lip, and Maxilla', Journal of Oral and Maxillofacial Surgery. 2010, vol. 68, No. 10, pp. 2513-2519.

(Continued)

*Primary Examiner* — Dinah Baria
(74) *Attorney, Agent, or Firm* — Innovation Capital Law Group, LLP; Vic Lin

(57) ABSTRACT

There is provided herein a bone anchored implant that is used to support a nasal prosthesis in patients with a missing external nose. The implant consists of central section (which is preferably generally triangular) suspended within the aperture of the nasal cavity by four fixation arms which extend radially to engage the surrounding maxillary bone. The triangular portion may support three fixation points, one at each corner of the triangular portion, which in turn, directly engage the nasal prosthesis either via magnets or mechanical locking interface. Extending radially from the triangular section, the four fixation arms may flatten to a (Continued)

clover leaf arrangement of three apertures which accommodate micro-screws that secure the implant to the surrounding maxillary bone.

18 Claims, 2 Drawing Sheets

(52) U.S. Cl.
CPC . *A61F 2002/2885* (2013.01); *A61F 2210/009* (2013.01); *A61F 2220/0041* (2013.01); *A61F 2230/0023* (2013.01)

(56) References Cited

U.S. PATENT DOCUMENTS

2011/0125091 A1* 5/2011 Abbate ............... A61M 31/002
 604/96.01
2013/0269165 A1 10/2013 Marotta

OTHER PUBLICATIONS

Buzayan, M. M. et al., 'Virtual Treatment Planning for Implant-Retained Nasal Prosthesis: A Clinical Report', The International Journal of Oral & Maxillofacial Implants. 2017, vol. 32, No. 6, pp. 1-4.

Chaturvedi, S. et al., 'Rehabilitation of Nose following Chemical Burn Using CAD/CAM Made Substructure for Implant Retained Nasal Prosthesis: A Clinical Report', Case Reports in Dentistry. 2017, vol. 2017, No. 2784606, pp. 1-7.

Ethunandan, M. et al., 'Implant-retained nasal prosthesis for reconstruction of large rhinectomy defects: the Salisbury experience', International Journal of Oral and Maxillofacial Surgery. 2010, vol. 39, No. 4, pp. 343-349.

International Search Report & Written Opinion dated May 22, 2019 from PCT Application No. PCT/AU2019/050107.

Scott, N. et al., 'The use of zygomatic implants for the retention of nasal prosthesis following rhinectomy: the Morriston experience', International Journal of Oral and Maxillofacial Surgery. 2016, vol. 45, No. 8, pp. 1044-1048.

Trevisiol, L. et al., 'Rehabilitation of a complex midfacial defect by means of a zygomaimplant-supported prosthesis and nasal epithesis: a novel technique', International Journal of Implant Dentistry. 2016, vol. 2, No. 1, p. 7.

* cited by examiner

ANCHORED IMPLANT FOR A NASAL PROSTHESIS

FIELD OF THE INVENTION

This invention relates generally to nasal prostheses and, more particularly, this invention relates to an anchored implant for a nasal prosthesis.

BACKGROUND OF THE INVENTION

The human nose occupies the central part of the face and is an essential appendage that provides the important function of smell and filters and humidifies the air we breathe. The nose also plays a central role in the aesthetics of the face. The nose can also support spectacles such as sunglasses or eyeglasses for the visually impaired.

In rare cases, the external nose may be missing due to trauma or following surgical resection for cancer or other destructive pathology. A missing external nose, which may include the nasal bridge, nasal dorsum and tip together with the alar and columella which surround the nasal apertures, results in a hideous deformity on the face which attracts negative reactions by others. The psychological impact of a missing external nose is devastating for the patient who invariably becomes a recluse.

While there are various surgical reconstructive procedures available to rebuild a missing external nose, often utilizing skin from the patient's forehead, the results are usually unpredictable and the natural aesthetics are difficult to recreate accurately.

Alternatively, prosthetic noses have been devised over the centuries that have had less than favourable outcomes because of the lack of suitable anchorage points around the nasal defect. Specifically, the bone surrounding the nasal aperture is very seven and, as such, conventional osseointegrated implants have had limited success.

The present invention seeks to provide an anchored implant for a nasal prosthesis, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

There is provided herein a new bone anchored implant that is used to support a nasal prosthesis in patients with a missing external nose. The implant consists of central section (which is preferably generally triangular) suspended within the aperture of the nasal cavity by four fixation arms which extend radially to engage the surrounding maxillary bone.

The triangular portion may support three fixation points, one at each corner of the triangular portion, which in turn, directly engage the nasal prosthesis either via magnets or mechanical locking interface. Extending radially from the triangular section, the four fixation arms may flatten to a clover leaf arrangement of three apertures which accommodate micro-screws that secure the implant to the surrounding maxillary bone.

The implant may be made of a medical grade titanium alloy or other such biocompatible metal or polymer that is directly anchored to the surrounding maxillary bone with titanium alloy micro-screws. The nasal prosthesis may be constructed separately from silicone rubber and directly attached to the implant via the three fixation points on the central triangular plate.

The prosthesis-implant attachment interface may include, but not be limited to, magnets, clips, screws, rotational and sliding locking mechanisms.

The design of the present implant takes is suitable for the thin bone surrounding the nasal aperture which we found can accommodates a maximum of about 12 micro-screws whilst being adequate to support the static weight of the nasal prosthesis as well as eye glasses that may be placed against the bridge of the prosthetic nose.

The implant can provided as a standardised device which can be adapted to the surrounding native bone at the time of surgery by bending malleable titanium fixation arms and choice of any of the available screw holes thereof. Alternatively, the implant can be customised using digital design overlayed on a patient's CT scan wherein the device is 3D printed to follow the precise contours of the surrounding bone.

The surgical procedure to install the implant involves dissecting and exposing the bony maxillary walls surrounding the nasal defect. The implant is then positioned so that the central triangular plate is properly aligned with the central part of the defect before the lateral arms are secured to the surrounding maxillary bone with up to 12 micro-screws. The surgical site is then given 7 days to heal before construction begins on the nasal prosthesis which is eventually attached to the implant frame via the three fixation point abutments.

The triangular positioning of the three fixation points prevents pivoting or rotational motion of the nasal prosthesis. The three fixation points firmly anchor the nasal prosthesis and provide support in three dimensions of space. The design of the implant also allows easy cleaning of the metal framework which encourages regular hygiene by the patient.

As such, with the foregoing in mind, in accordance with one aspect, there is provided an anchored implant for a nasal prosthesis comprising: a central section supporting three nasal prosthesis fixation points at a respective superior vertex and two inferior lateral vertices; four fixation arms comprising: two superior fixation arms spanning substantially laterally from the superior vertex; two inferior arms spanning substantially laterally from respective inferior lateral vertices.

The triangular section may define a central void therethrough.

The central section may be substantially triangular.

The implant may be sized such that the four fixation arms attach to the maxilla when implanted.

Each fixation arm may terminate at a fixation terminus having at least one aperture therein for microscrews.

The at least one aperture may be three apertures.

The three apertures may be substantially symmetrically arranged with respect to an elongate axis of each respective fixation arm.

The fixation terminus may be flattened.

The fixation terminus may be widened.

Each fixation arm may transition posteriorly with respect to the central section.

Each fixation arm may transition from a first section being substantially parallel with respect to a cross sectional plane of the central section to a second section being angled with respect to the cross-sectional plane of the central section.

The second section may be angled at approximately 45° with respect to the cross-sectional plane of the central section.

The second section leads to a fixation terminus and wherein the second section and the fixation terminus may be substantially parallel.

The second section may be flattened.

The fixation points may be magnetic attachment fixation points.

Each fixation point may comprise a buttress socket.

The buttress sockets may be located anteriorly of the central section.

The buttress sockets may be parallel.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 2:
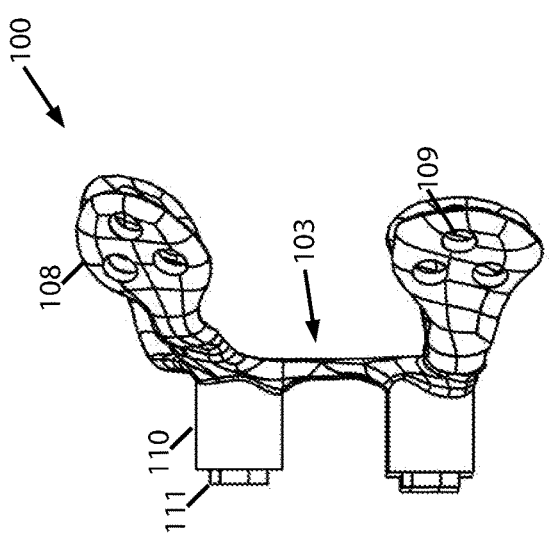
FIG. 2 shows a side elevation view of the implant.
Figure 4:
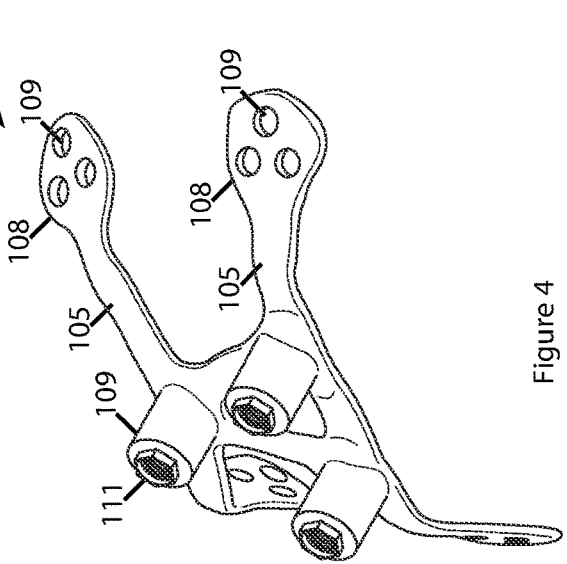
FIG. 4 shows a bottom perspective view of the implant.
Figure 1:
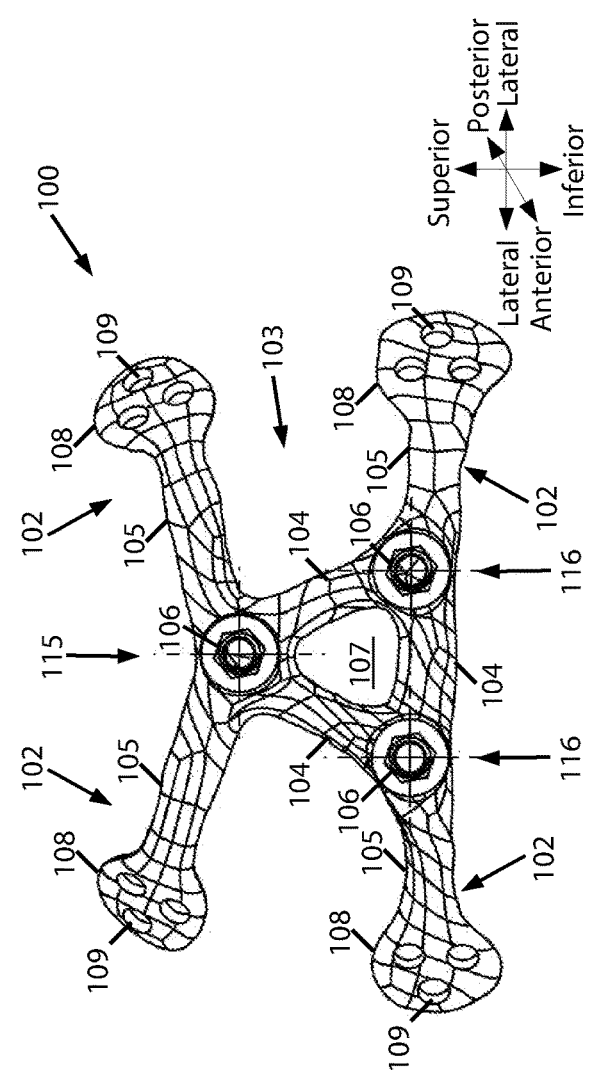
FIG. 1 shows a top view of an anchored implant four nasal prosthesis in accordance with an embodiment.

FIG. 1 shows a top view of an anchored implant 100 for a nasal prosthesis in an embodiment which, for orientational convenience, will be described with reference to the orientational axes provided in FIG. 1 defining top/superior, bottom/inferior, side/lateral, front/anterior and rear/posterior reference points.

The implant 100 may be integrally formed of biocompatible material such as titanium.

The implant 100 comprises a central section 103 supporting at least three nasal prosthesis fixation points 106. In a preferred embodiment, the implant 100 has three nasal prosthesis fixation points 106 at a respective superior vertex 115 and two inferior lateral vertices 116.

Once the implant 100 is anchored, a nasal prosthesis (not shown) is affixed to the implant 100 at the fixation points 106.

In the preferred embodiment shown, the central section 103 is substantially triangular, thereby minimising cross-sectional area between the fixation points 106, thereby maximising airflow through the nasal cavity. Furthermore, in an embodiment, the triangular section 103 comprises a triangular arrangement of struts 104 spanning between the vertices 115, 116, thereby defining a central void 107 there through. Such configuration minimises cross-sectional area of the implant 100 and facilitates breathing therethrough.

In embodiments, the fixation points 106 may be magnetically attachable fixation points. In alternative embodiments as is substantially shown in FIG. 3, the fixation points 106 may comprise buttresses 110 each defining a threaded socket 111 therein. Each buttress 110 may have a hex nut formation surrounding the rim of the threaded socket 111. The buttresses 110 may be located anteriorly with respect to the central section 103 and, in the embodiment shown in FIG. 3, may be substantially parallel.

The implant 100 further comprises at least four fixation arms 102. In a preferred embodiment, the implant 100 comprises four fixation arms 102. The fixation arms 102 comprise two superior fixation arms spanning substantially laterally from the superior vertex 115. Furthermore, the fixation arms 102 comprise two inferior arms each spanning laterally from respective inferior lateral vertices 116.

Figure 7:
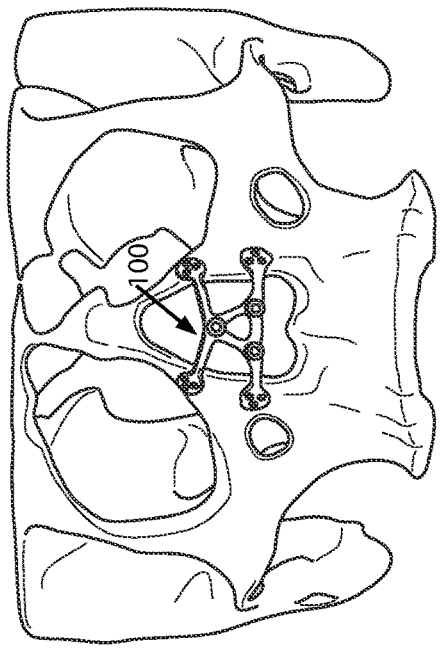
FIGS. 5-7 show respective top perspective, side and front views of the implant affixed to the maxilla.
Figure 5:
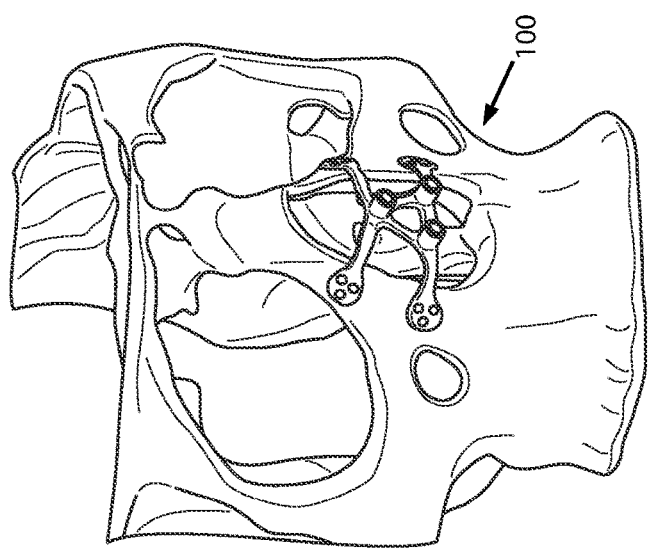
Figure 6:

The implant 100 is sized and shaped such that the four fixation arms 102 are able to reach and affix to the maxilla as is substantially shown in FIGS. 5-7.

Each fixation arm 102 terminates at a fixation terminus 108 having at least one aperture 109 therethrough for microscrews. In the embodiment shown, each fixation terminus 108 comprises three apertures 109.

Furthermore, in embodiments, the apertures 109 may be symmetrically arranged with respect to an elongate axis of each fixation arm 102 to enhance fixation stability. Specifically, in the embodiment shown, the apertures 109 comprise a distal aperture locating on the elongate axis and a pair of proximal apertures 109 located respectively adjacent the elongate axis.

Figure 3:
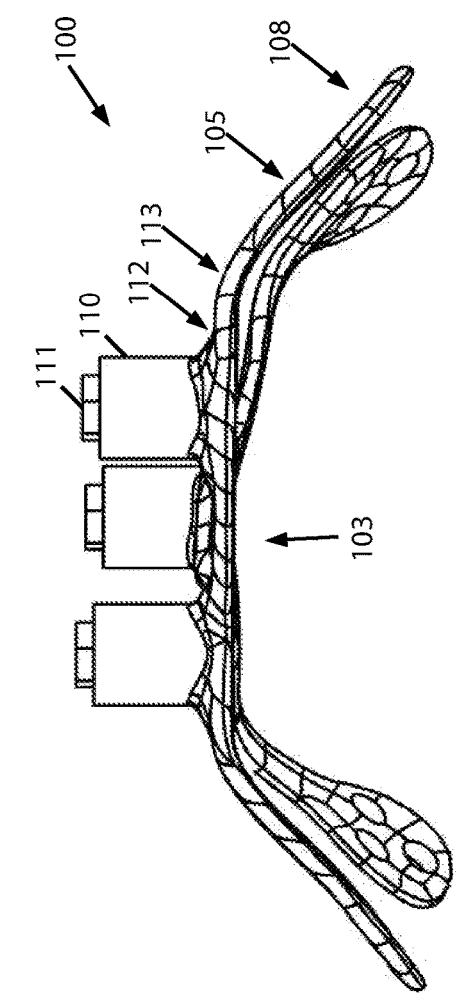
FIG. 3 shows an inferior view of the implant.

As can be especially appreciated from FIG. 3, each fixation terminus 108 may be flattened to increase the surface contact area against the maxilla and, furthermore, preferably widened so as to allow for appropriate spacing apart of the apertures 109.

As is further illustrated in FIG. 3, each fixation arm 102 transitions posteriorly with respect to the central section 103. Specifically, each fixation arm 102 transitions from a first section 112 being substantially parallel with respect to a cross-sectional plane of the central section 103 to a second section 105 which is angled with respect to the cross-sectional plane. In embodiments, the second section 105 may be angled at approximately 45° with respect to the central section 103.

As is also shown in FIG. 3, the second section 115 and the fixation terminus 108 may be substantially parallel.

Furthermore, in a preferred embodiment, the second section 105 is itself also flattened as shown in FIG. 3.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. An anchored implant for a nasal prosthesis comprising:
 a central section supporting three nasal prosthesis fixation points at a respective superior vertex and two inferior lateral vertices of the central section; and
 four fixation arms comprising:
  two superior fixation arms spanning substantially laterally from the superior vertex; and
  two inferior arms each spanning substantially laterally from respective inferior lateral vertices, wherein each of the fixation points comprises a buttress socket.

2. An anchored implant as claimed in claim 1, wherein the central section is substantially triangular.

3. An anchored implant as claimed in claim 2, wherein the triangular section defines a central void therethrough.

4. An anchored implant as claimed in claim 1, wherein the implant is sized such that the four fixation arms attach to the maxilla when implanted.

5. An anchored implant as claimed in claim 1, wherein each fixation arm terminates at a fixation terminus having at least one aperture therein for microscrews.

6. An anchored implant as claimed in claim 5, wherein the at least one aperture is three apertures.

7. An anchored implant as claimed in claim 6, wherein the three apertures are substantially symmetrically arranged with respect to an elongate axis of each respective fixation arm.

8. An anchored implant as claimed in claim 5, wherein the fixation terminus is wider than a width of each respective fixation arm.

9. An anchored implant as claimed in claim 5, wherein the fixation terminus is flattened.

10. An anchored implant as claimed in claim 1, wherein each fixation arm transitions posteriorly with respect to the central section.

11. An anchored implant as claimed in claim 10, wherein each fixation arm transitions from a first section being substantially parallel with respect to a cross sectional plane of the central section to a second section being angled with respect to the cross-sectional plane of the central section.

12. An anchored implant as claimed in claim 11, wherein the second section is angled at approximately 45° with respect to the cross-sectional plane of the central section.

13. An anchored implant as claimed in claim 11, wherein the second section leads to a fixation terminus and wherein the second section and the fixation terminus are substantially parallel.

14. An anchored implant as claimed in claim 11, wherein the second section is flattened.

15. An anchored implant as claimed in claim 1, wherein the buttress sockets are located anteriorly of the central section.

16. An anchored implant as claimed in claim 15, wherein the buttress sockets are disposed on a respective buttress for each fixation point, each buttress extending anteriorly from the central portion, wherein the side portions of each buttress are parallel.

17. A method for providing a support for a nasal prosthesis, the method comprising:
 obtaining an anchored implant as claimed in claim 1; and
 affixing the fixation arms of the anchored implant to the maxilla.

18. An anchored implant for a nasal prosthesis comprising:
 a central section supporting three nasal prosthesis fixation points at a respective superior vertex and two inferior lateral vertices of the central section; and
 four fixation arms comprising:
 two superior fixation arms spanning substantially laterally from the superior vertex; and
 two inferior arms each spanning substantially laterally from respective inferior lateral vertices, wherein
 each of the fixation points are magnetic attachment fixation points.

* * * * *